United States Patent [19]
Falbo, Sr.

[11] Patent Number: 5,184,363
[45] Date of Patent: Feb. 9, 1993

[54] SUPPORT BED WITH DROP-OUT SECTIONS FOR MEDICAL ANALYSIS

[75] Inventor: Michael G. Falbo, Sr., Gladstone, Mo.

[73] Assignee: American Echo, Inc., Kansas City, Mo.

[21] Appl. No.: 883,566

[22] Filed: May 15, 1992

[51] Int. Cl.⁵ .............................................. A61C 7/00
[52] U.S. Cl. ......................................... 5/601; 5/937; 5/600
[58] Field of Search ................... 5/600, 601, 602, 613, 5/937

[56] References Cited

U.S. PATENT DOCUMENTS

| | | | |
|---|---|---|---|
| 222,455 | 3/1880 | Adams | 5/937 X |
| 395,001 | 12/1888 | Russell . | |
| 1,040,795 | 10/1912 | Skeffington | 5/613 X |
| 1,274,851 | 8/1918 | Byrd | 5/613 |
| 1,891,599 | 12/1932 | Kushner | 5/613 |
| 2,103,693 | 12/1937 | Pohl . | |
| 2,897,029 | 7/1959 | Maisel . | |
| 3,265,432 | 8/1966 | Tabbert . | |
| 3,652,851 | 3/1972 | Zaalberg . | |
| 3,795,018 | 3/1974 | Broaded | 5/613 |
| 3,973,126 | 8/1976 | Redington et al. . | |
| 4,620,333 | 11/1986 | Ritter . | |
| 4,973,034 | 11/1990 | Michele . | |

OTHER PUBLICATIONS

TM: Echo Table and Echo Bed: Specifications and Ordering Information; American Echo Incorporate 419 E. 31st Street; Kansas City, Missouri 64108.

*Primary Examiner*—Michael F. Trettel
*Attorney, Agent, or Firm*—Hovey, Williams, Timmons & Collins

[57] ABSTRACT

A patient-supporting bed (20) especially adapted for cardiac sonography is provided which includes a frame assembly (22) and mattress (24) which are configured to present a pair of marginal, axially offset access openings (49, 54) and a corresponding pair of shiftable bed filler sections (26, 28) disposed within the openings (49, 54). Each of the sections (26, 28) includes a latching assembly (86) serving to normally maintain each of the sections (26, 28) in an upper, generally horizontal position so that the bed (20) presents a generally horizontal and uninterrupted patient-supporting top surface. A patient is positioned on the bed with the patient's heart region located generally above the first filler section (26). The sonographer then manipulates the associated latching assembly (86), allowing the section (26) to pivot downwardly and thus expose an access opening (49). The second filler section (28) is similarly manipulated to expose the opening (54). The sonographer may then stand in the opening (54), or sit on mattress (24) with the sonographer's legs within the opening (54), and sonographic probe(s) can be readily positioned for rapid and accurate diagnosis. After the sonography is completed, the respective sections (26, 28) are returned to their horizontal positions. Pinching of the patient during return movement of the section (26) is precluded by provision of a flexible cover (82a) disposed over the juncture between the section (26) and mattress (24).

9 Claims, 3 Drawing Sheets

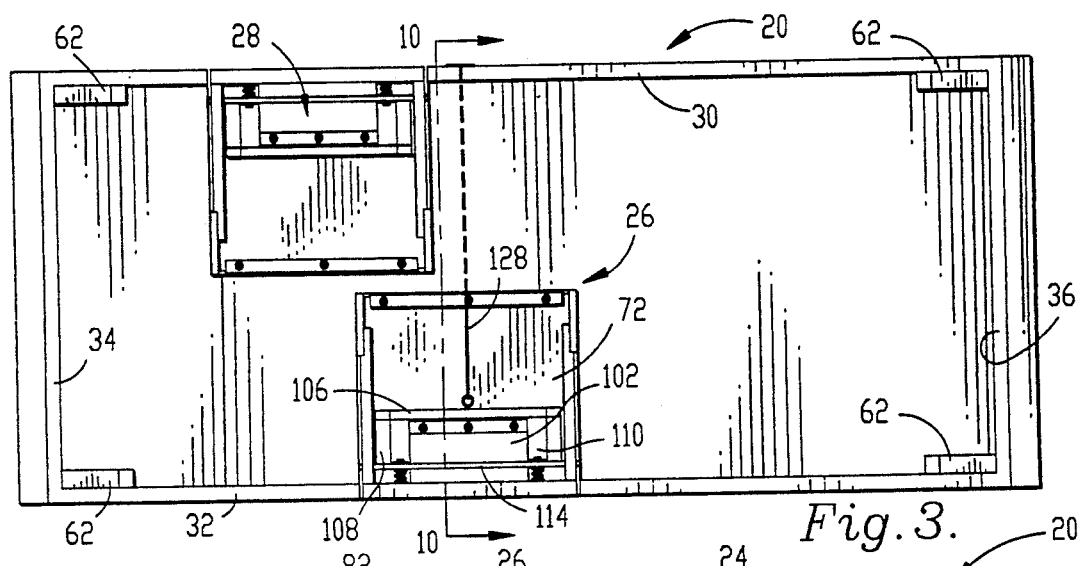
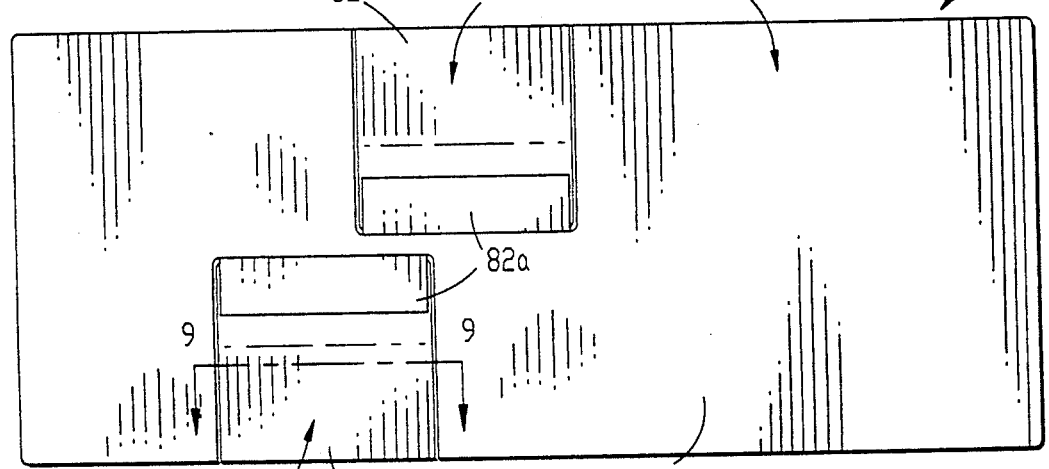
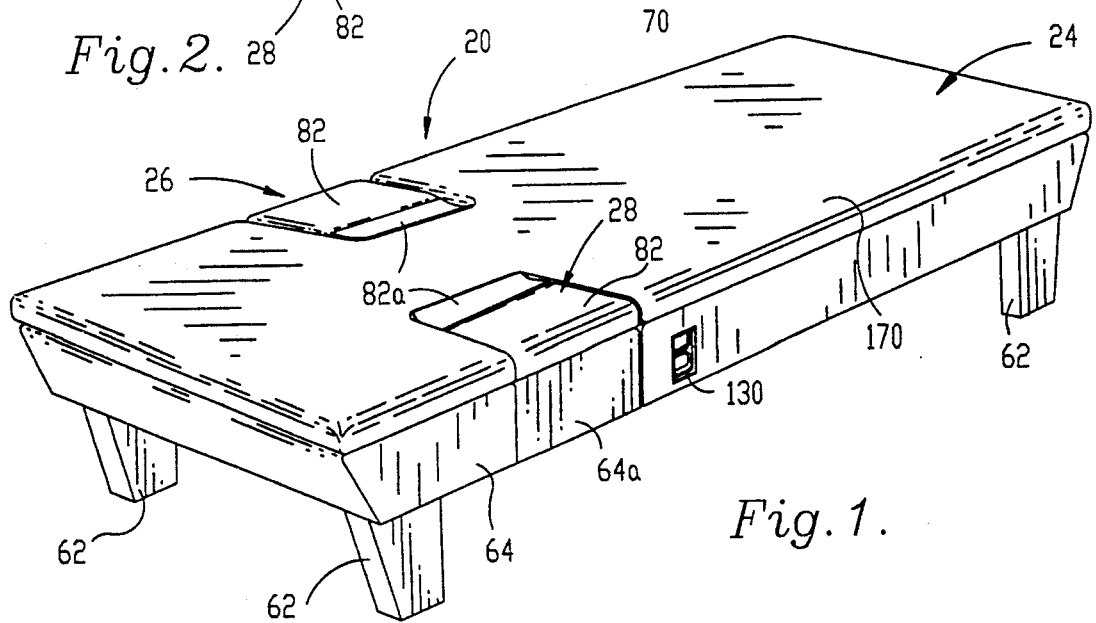

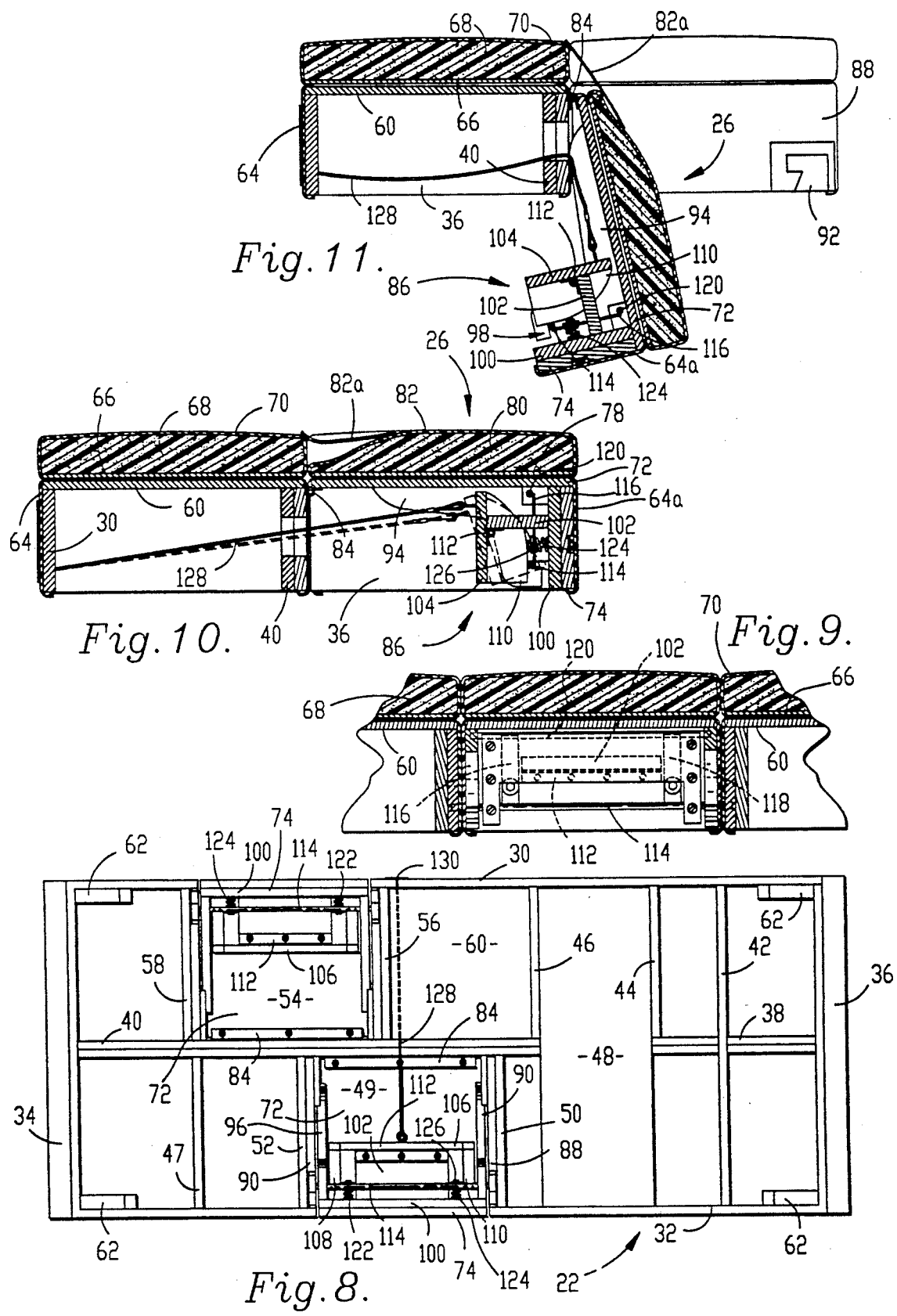

SUPPORT BED WITH DROP-OUT SECTIONS FOR MEDICAL ANALYSIS

BACKGROUND OF THE INVENTION

1. Field of the Invention

The present invention is broadly concerned with an improved patient-supporting bed that facilitates various diagnoses, and particularly echo cardiography scans, upon a person lying upon the bed. More particularly, it is concerned with such a diagnostic bed that includes a hingedly mounted, selectively disengageable, drop-out bed section strategically located for permitting easy sonographic diagnosis of a patient. In particularly preferred forms, an anti-pinching flexible cover is disposed over the juncture between the drop-out section and bed proper, and a second, laterally spaced and axially offset drop-out section is optionally provided that can be lowered to present an opening accommodating the legs of a person performing the diagnosis, thereby facilitating the sonographic examination.

2. Description of the Prior Art

Diagnosis of cardiac irregularities often involves a treadmill test, wherein a patient exercises on a treadmill in order to increase his or her heartbeat to an elevated rate where an abnormality may be detected. Experience has proved that treadmill (exercise EKG) testing alone will not give an accurate diagnosis for a relatively large number of patients, i.e., even though the heart rate is elevated, an extant problem will not be detected. This is particularly the case with women patients.

As a consequence, it has become a common practice to perform cardiac sonography (also known as an echo cardiography scan) on a patient immediately after a treadmill test is completed and while the patient's heart rate is still elevated. This combined diagnostic technique has proven to be very successful in correctly ascertaining the true condition of the patient's heart. However, in order to be optimum, it is very necessary that two conditions be met. First the cardiac sonography be completed in as short a period of time as possible after the treadmill test is concluded. Second, the patient should be examined while lying on the left side (left lateral). Otherwise, the sonography will yield less accurate or erroneous results. Every second is important because the heart fully recovers from the effects of exercise in about two minutes.

In general, cardiac sonography is accomplished by placing a person on a diagnostic bed, lying on his or her left side. A drop-out access door or section is provided in the bed adjacent the heart region, and can be lowered to provide an access opening allowing the sonographer to place the sonography probe(s) at the various positions required for the diagnosis. The drop-out door is essential because patients will not position themselves properly over a space or hole. Further, the drop-out door is equipped with a latch that is easily and quickly opened requiring only one hand to accomplish. At the conclusion of the sonographic examination, the drop-out section is raised back to its original position, in order to allow the patient to safely rise from the bed. If the patient attempts to arise while the drop-out door is lowered, a danger is presented because the patient's hand and arm may slip into the bed opening as the patient attempts to push himself upwardly from the surface of the bed.

Use of diagnostic beds of this type presents a number of problems. In the first place, many cardiac patients are morbidly obese, and it can be very difficult for the sonographer to properly position the sonography probe(s) beneath the patient adjacent the heart region. Many sonographers have been forced to stand, sit or straddle in unnatural, uncomfortable positions on or adjacent the diagnostic bed astride the patient, and attempt to reach across the patient's body to position the probe(s) for proper diagnosis. This can be very difficult with obese patients, particularly under the time constraint of performing the diagnosis in the short applicable time after a treadmill test.

Secondly, when the drop-out section is returned to its upper horizontal position at the conclusion of the sonographic examination, the patient may be pinched between the shiftable section and the bed proper. Here again, this problem is especially acute with obese patients.

There is accordingly a real and unsatisfied need for an improved diagnostic bed especially adapted to overcome the problems of prior beds of this character in the context of cardiac sonography examinations.

SUMMARY OF THE INVENTION

The present invention overcomes the difficulties outlined above, and provides an improved diagnostic patient support bed that facilitates movement of the sonographer in and around a recumbent patient on the bed, while also eliminating pinching of the patient.

Broadly speaking, the support bed of the invention includes an elongated, generally disposed bed presenting an uppermost bed surface and either one or a pair of elongated, laterally spaced apart first and second side margins and transverse end margins. Structure is provided for defining opposed, first and second openings in the bed surface and respectively adjacent a corresponding side margin. The first opening is located and sized for permitting sonographic diagnosis of a patient lying on the bed, whereas the second opening is located and sized for accommodating the legs or other aspect of a person performing the diagnosis. A first bed filler section of a size to substantially fill the first opening is provided, and is mounted for movement between an upper position wherein the first bed filler section presents, with the overall bed surface, a substantially uninterrupted patient-supporting area, along the length of the bed and adjacent the first side margin. The first bed filler section may also be moved to a lower position at least partially below the upper bed surface in order to create an access opening facilitating sonographic diagnosis of a recumbent patient.

In particularly preferred forms, the second opening is likewise provided with a corresponding second bed filler section that is movable between a similar upper and lower position. The second opening is advantageously laterally spaced and axially offset from the first opening.

The first bed filler section is preferably hingedly secured tot he bed by means of a recessed hinge located well away form the upper surface of the bed and section. Moreover, a flexible cover is provided between the uppermost bed surface and bed filler section for bridging and covering the hinge region, thereby eliminating the possibility of pinching of a patient when the section is returned to its upper position at the conclusion of a sonographic examination.

BRIEF DESCRIPTION OF THE DRAWINGS

FIG. 1 is an isometric view of diagnostic patient support bed in accordance with the invention;

FIG. 2 is a plan view thereof;

FIG. 3 is a bottom view thereof;

FIG. 8 is a bottom view of the bed framework and mechanisms supporting the drop-out filler sections of the bed;

FIG. 9 is a vertical sectional view taken along line 9—9 of FIG. 2;

FIG. 10 is a vertical sectional view taken along line 10—10 of FIG. 3, with the operation of the filler section latch being illustrated in phantom; and FIG. 11 is a sectional view similar to that of FIG. 10, but depicting the drop-out filler section in its lower position.

DETAILED DESCRIPTION OF THE PREFERRED EMBODIMENT

Figure 7:
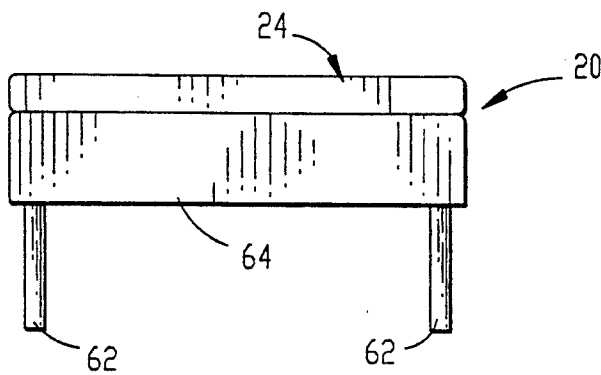
FIG. 7 is an end elevational view illustrating the end opposite that of FIG. 6.
Figure 6:
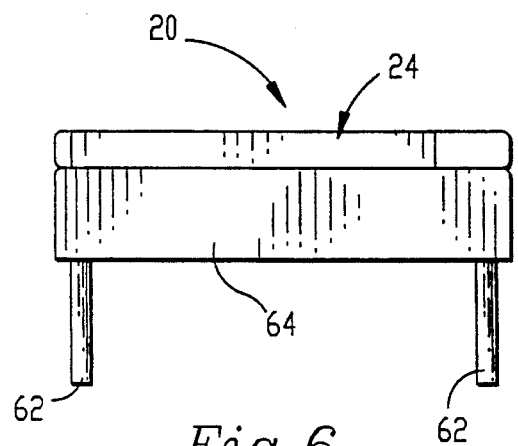
FIG. 6 is an end elevational view thereof.
Figure 5:
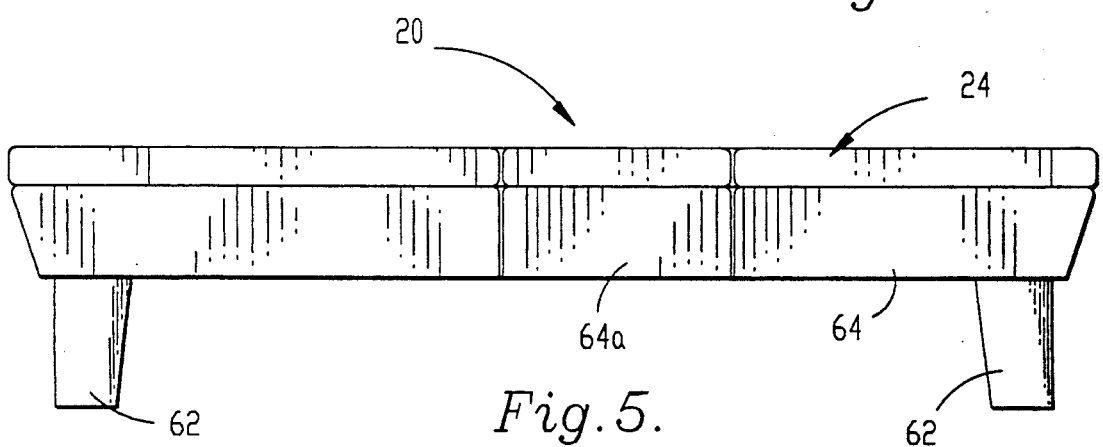
FIG. 5 is a side elevational view of the side opposite that depicted in FIG. 4.
Figure 4:
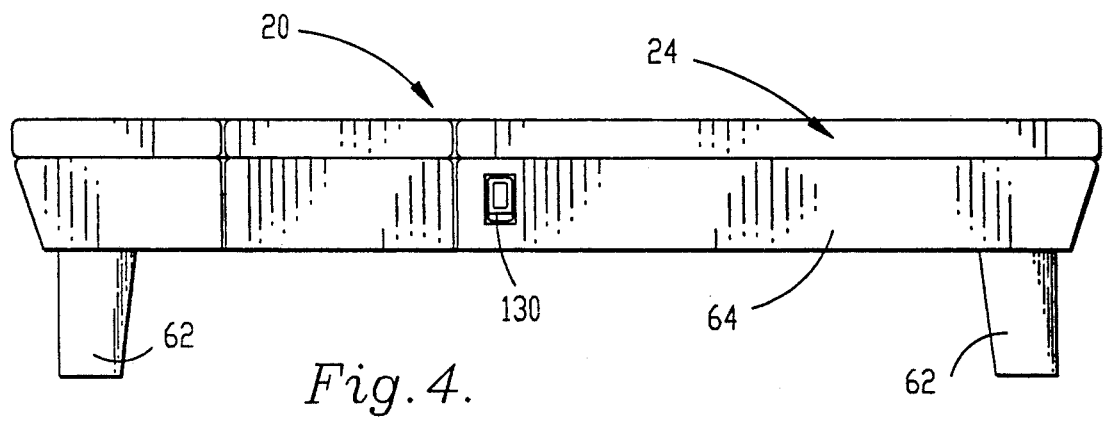
FIG. 4 is a side elevational view thereof, illustrating the side remote from the patient-supporting area of the bed.

Turning now to the drawings, a patient-supporting bed 20 is illustrated that broadly includes a lower frame assembly 22 supporting an upper, elongated, generally horizontally disposed mattress 24, as well as first and second, generally L-shaped shiftable bed filler sections 26, 28.

In more detail, the frame assembly 20 includes a wooden framework presenting elongated, apertured side rails 30, 32, end rails 34, 36, a short, two-piece central rail 38 adjacent the foot of the bed 20, a longer, two-piece, apertured central rail 40 extending from the head of bed 22, as well as transverse reinforcing rails 42, 44 46 and 47, and a transverse reinforcing beam 48. The overall frame 22 also presents a first, generally square opening 49 defined between side rail 32 and central rail 40, and bounded by transverse sidewalls 50, 52. Additionally, a second, generally square opening 54 is defined between side rail 32 and central rail 40, and is bounded by sidewalls 56, 58.

The frame assembly 22 is completed by provision of stationary wooden top plate 60, which is disposed over the entirety of the frame except for the openings 49, 54. Also, the frame 22 is supported by corner-mounted legs 62 as illustrated, and leather-like upholstery material 64 is applied to the exterior surfaces of the frame.

The mattress 24 is situated atop plate 60 and presents a lowermost reinforcing board 66, resilient padding 68, and a covering sheath of upholstery material 70. As in the case of plate 60, the mattress 24 covers the entirety of the bed, save for the openings 49 and 54. Conventional means (not shown) are provided for securing the stationary mattress 24 in place on plate 60.

The first bed filler section 26 is in the form of a generally L-shaped body presenting an upper plate 72 as well as depending side plate 74, with the latter being covered by material 64a. As best seen in FIGS. 1 and 2, the filler 26 is sized to essentially fill the opening 49 in frame assembly 22. A mattress pad 76 is positioned atop plate 72 and includes a lower reinforcing board 78, padding 80 and cover 82. As best in FIGS. 10 and 11, the padding 80 is reduced in thickness adjacent the inboard edge of plate 72, whereas the cover 82 extends from the full thickness region of the padding 80 to the full thickness margin of the padding 68. Thus, in the upper position of the filler 26 illustrated in FIG. 10, an inboard flexible section 82a of the cover 82 extends leftwardly and is connected to the cover material 70 of the adjacent stationary mattress 24.

The first filler section 26 is pivotally secured to the bed proper by means of a hinge 84 interconnecting central rail 40 and top plate 72. The entire filler section 26 is moreover shiftable between an upright position wherein plate 72 is generally horizontal and aligned with stationary plate 60 (FIG. 10) and a lowered position as illustrated in FIG. 11.

The filler section 26 is normally maintained in its upper, FIG. 10 position by means of a latching assembly broadly referred to by the numeral 86. Assembly 86 includes a pair of laterally spaced apart latching boards 88, 90 each presenting a latch opening 92 (see FIG. 11). In addition, a pair of arcuate reinforcing elements 94, 96 are provided respectively adjacent the latching boards 88, 90 and secured tot he plates 72, 74; the elements 94, 96 have respective notches 98 adjacent the outboard ends thereof.

An upright reinforcing board 100 is secured to the inner face of side plate 74, and has an inwardly extending, central, generally horizontal mounting plate 102 secured thereto. A generally U-shaped rocker 104 is connected to the inboard end of mounting plate 102 and includes an upright backing plate 106, together with a pair of outwardly extending, arcuate side boards 108, 110 which straddle mounting plate 102. A hinge 112 serves to connect plate 106 to mounting plate 102 and permit limited pivoting movement thereof about a horizontal axis.

An elongated latching bar 114 extends laterally across the filler section 26 and is located within the notches 98. The outboard ends of the bar 114 are received within the latch openings 92; when the section 26 is in its upper FIG. 10 position, the ends of bar 114 are located within the inboard, horizontal regions of the openings 92.

The bar 114 is urged towards its latching position by means of a pair of elongated, vertically extending, laterally spaced apart metallic straps 116, 118 which engage the bar 114 adjacent their lowermost ends. The straps 116, 118 are secured adjacent their upper ends to an elongated, transversely extending rod 120 as shown, and are urged inwardly by means of a pair of coil springs 122, 124. Each of the springs 122, 124 is affixed to board 100 by means of corresponding bolts 126.

The latching assembly 86 may be remotely operated by means of lanyard 128 which is connected to the inboard face of plate 106 and extends transversely across frame assembly 22 through central rail 40. The lanyard 128 terminates at side rail 30, and an external pull handle 130 (see FIG. 1) is provided within the side rail 30 and connected to the lanyard 128.

The second bed filler section 28 is identical with section 26, except for the fact that the section 28 is not provided with a remote actuating mechanism, i.e., it has no lanyard 128 or operating handle 130. Accordingly, a detailed discussion of the section 28 is unnecessary, and like reference numerals have been applied to like parts.

In the use of bed 20, the first and second filler sections 26, 28 are normally placed in their uppermost positions, so that the bed presents a substantially uninterrupted patient-supporting area along the length thereof. After a treadmill test, a patient is immediately placed on the bed 20, with the patient lying on his or her left side, and with the patient's heart region above section 26.

After the patient is properly placed on the bed 20, the sonographer then grasps handle 130 and pulls lanyard 128 in order to drop the first filler section 26 to its lowered position and clear opening 49. Pulling lanyard 128 leftwardly as viewed in FIG. 10 correspondingly pivots backing plate 106 as shown in phantom, with the effect that side boards 108, 110 engage latching bar 114 and push it rightwardly until the latching bar clears the horizontal ledges of the latch openings 92. When the latching bar 114 is moved to this extent, the section 26 drops downwardly under the influence of gravity, this being accommodated by the recessed hinge 84. In this respect, it will further be seen (FIG. 11) that the cover section 82a serves to bridge the reduced thickness portion of padding 80 and the adjacent corner of cover 70, thereby covering the open area between the inner end of the section 26 and the stationary mattress 24. The section 82a thus prevents any portion of the patient's skin from entering the region adjacent hinge 84 where pinching could occur.

The sonographer next drops the second filler section 28 to its lowered position, in order to open access opening 54. This operation is accomplished simply by reaching under side plate 74 and reinforcing board 100, grasping bar 114, and pulling the same outwardly until the bar clears the horizontal legs of the latch openings 92, whereupon the section 28 pivots downwardly as described with reference to section 26. The rocker assembly described with reference to section 26 can be provided with the section 28, in order to afford remote operation. However, in the manual disengagement procedure described, this structure is unnecessary.

After the section 28 is dropped to its lower position, the sonographer may stand in the opening 54, or sit on mattress 24 adjacent the patient with the sonographer's legs within this opening. In either case, the sonographer can then more readily reach over the patient's body for proper positioning of the sonography probe(s), without unnatural twisting or strain.

At the discretion of the sonographer, it is also possible to begin the procedure by dropping filler section 28 followed by dropping filler section 26. It is also possible to begin the procedure with filler section 28 in the open (dropped) position.

After the sonographic examination is completed, the sections 26 and 28 are lifted back to their respective horizontal positions until the latching bars 114 thereof are positioned within the associated latch openings 92. During raising of the section 26, the patient would normally still be lying on bed 20. However, the cover section 82a prevents pinching of the patient during elevation and relatching of the section 26, inasmuch as the juncture between the section 26 and the bed proper is covered at all times. After the first and second filler sections are relatched, the patient can then arise from the bed 20 in the usual fashion.

I claim:

1. A diagnostic patient support bed, comprising:
an elongated, generally horizontally disposed bed presenting an uppermost bed surface, a pair of elongated, laterally spaced apart first and second side margins, and a pair of axially spaced, transversely extending end margins;
structure defining opposed, first and second openings in said bed surface and respectively adjacent a corresponding side margin,
said first opening being located and sized for permitting sonographic diagnosis of a patient lying on said bed surface,
said second opening being located and sized for accommodating the legs of a person performing said sonographic diagnosis;
a first bed filler section sized to substantially fill said first opening; and
means mounting said first bed filler section to said bed for movement of the first bed filler section between an upper position where the first bed filler section presents, with said bed surface, a substantially uninterrupted patient-supporting area along the length of the bed surface adjacent said first side margin, and a lowered position wherein the first bed filler section is disposed at least partially below said bed surface in order to create an access opening facilitating sonographic diagnosis of a patient lying on said area,
said diagnostic patient support bed including a second bed filler section sized to fit within said second opening, there being means mounting said second bed filler section for selective lowering thereof below the bed surface in order to create a region for accommodating the legs of a person performing the sonographic diagnosis.

2. The diagnostic patient support bed of claim 1, said first and second openings respectively communicating with a corresponding side margin.

3. The diagnostic patient support bed of claim 1, said mounting means including structure for pivotally supporting said first bed section for movement thereof between said upper and lower positions.

4. The diagnostic patient support bed of claim 3, including selectively disengageable latch means for normally maintaining said first bed filler section in said upper position thereof.

5. The diagnostic patient support bed of claim 4, including operating means coupled with said latch means for permitting disengagement of the latch means from a position adjacent said second side margin of said bed.

6. The diagnostic patient support bed of claim 3, said first bed filler section being recessed adjacent the point of pivotal connection thereof to said bed, there being a flexible cover extending between said uppermost bed surface and the first bed filler section for bridging the juncture between the uppermost bed surface and first bed filler section when the first bed filler section is in the lower position thereof, in order to prevent pinching of a patient when the first bed filler section is returned to the upper position thereof.

7. A diagnostic patient support bed, comprising:
an elongated, generally horizontally disposed bed presenting an uppermost bed surface, a pair of elongated, laterally spaced apart first and second side margins, and a pair of axially spaced, transversely extending end margins;
structure defining a first opening in said bed surface and respectively adjacent said first side margin,
said first opening being located and sized for permitting sonographic diagnosis of a patient lying on said bed surface;
a first bed filler section sized to substantially fill said first opening; and means mounting said first bed filler section to said bed for pivotal movement of the first bed filler section between an upper position where the first bed filler section presents, with said bed surface, a substantially uninterrupted patient-supporting area along the length of the bed surface adjacent said first side margin, and a lowered position wherein the first bed filler section is disposed at least partially below said bed surface in order to create an access opening facilitating sonographic diagnosis of a patient lying on said area, said first bed filler section being recessed adjacent the point of pivotal connection thereof to said bed, there being a flexible cover extending between said uppermost bed surface and the first bed filler section for bridging the juncture between the uppermost bed surface and first bed filler section when the first bed filler section is in the lower position thereof, in order to prevent pinching of a patient when the first bed filler section is returned to the upper position thereof.

8. The diagnostic patient support bed of claim 7, said mounting means including hinge structure located at the joint between said opening-defining structure and said first bed filler section, at a point beneath said flexible cover when the latter is bridging said juncture.

9. A diagnostic patient support bed, comprising:

an elongated, generally horizontally disposed bed presenting an uppermost bed surface, a pair of elongated, laterally spaced apart first and second side margins, and a pair of axially spaced, transversely extending end margins;

structure defining opposed, first and second openings in said bed surface and respectively adjacent a corresponding side margin, said first opening being located and sized for permitting sonographic diagnosis of a patient lying on said bed surface, said second opening being located and sized for accommodating the legs of a person performing said sonographic diagnosis;

a first bed filler section sized to substantially fill said first opening; and means mounting said first bed filler section to said bed for movement of the first bed filler section between an upper position where the first bed filler section presents, with said bed surface, a substantially uninterrupted patient-supporting area along the length of the bed surface adjacent said first side margin, and a lowered position wherein the first bed filler section is disposed at least partially below said bed surface in order to create an access opening facilitating sonographic diagnosis of a patient lying on said area, said mounting means including structure for pivotally supporting said first bed section for movement thereof between said upper and lower positions, support bed including selectively disengageable latch means for normally maintaining said first bed filler section in said upper position thereof and including operating means coupled with said latch means for permitting disengagement of the latch means from a position adjacent said second side margin of said bed; and said fist bed filler section being recessed adjacent the point of pivotal connection thereof to said bed, there being a flexible cover extending between said uppermost bed surface and the first bed filler section for bridging the juncture between the uppermost bed surface and first bed filler section when the first bed filler section is in the lower position thereof, in order to prevent pinching of a patient when the first bed filler section is returned to the upper position thereof.

* * * * *